United States Patent
Murata et al.

(10) Patent No.: US 8,481,660 B2
(45) Date of Patent: *Jul. 9, 2013

(54) MIXTURE OF FLUOROALKYL ALCOHOL-UNSATURATED CARBOXYLIC ACID DERIVATIVES, POLYMER OF THE MIXTURE, AND WATER-AND OIL-REPELLENT CONTAINING THE POLYMER AS ACTIVE INGREDIENT

(75) Inventors: Seiichiro Murata, Ibaraki (JP); Masayosi Horiuti, Ibaraki (JP); Katsuyuki Sato, Ibaraki (JP); Satoshi Kurihara, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 354 days.

This patent is subject to a terminal disclaimer.

(21) Appl. No.: 12/863,465

(22) PCT Filed: Jan. 20, 2009

(86) PCT No.: PCT/JP2009/050745
§ 371 (c)(1),
(2), (4) Date: Jul. 19, 2010

(87) PCT Pub. No.: WO2009/093568
PCT Pub. Date: Jul. 30, 2009

(65) Prior Publication Data
US 2010/0292393 A1    Nov. 18, 2010

(30) Foreign Application Priority Data

Jan. 24, 2008  (JP) ................................. 2008-013386
May 29, 2008  (JP) ................................. 2008-140903
May 29, 2008  (JP) ................................. 2008-140904

(51) Int. Cl.
*C08F 18/20*    (2006.01)

(52) U.S. Cl.
USPC ........... 526/245; 524/544; 524/805; 560/211; 560/212; 560/223; 560/225

(58) Field of Classification Search
USPC .................. 524/544, 805; 526/245; 560/211, 560/212, 223, 225
See application file for complete search history.

(56) References Cited

U.S. PATENT DOCUMENTS

| 3,393,186 A * | 7/1968 | Groves ........................ 526/245 |
| 3,625,929 A * | 12/1971 | Stump et al. .................. 526/246 |
| 5,739,380 A * | 4/1998 | Lui et al. ...................... 560/220 |
| 2006/0025625 A1* | 2/2006 | Sato et al. .................... 560/223 |
| 2010/0288971 A1* | 11/2010 | Murata et al. ............ 252/182.12 |

FOREIGN PATENT DOCUMENTS

| GB | 1404351 A | * 8/1975 |
| JP | 44-1216 B1 | 1/1969 |
| JP | 46-5447 B1 | 2/1971 |
| JP | 63-22530 A | 1/1988 |
| JP | 2000-038361 A | 2/2000 |
| JP | 2003-012588 A | 1/2003 |
| WO | WO 2004/005708 A1 | 4/2004 |

OTHER PUBLICATIONS

Dmowski, W. et al., "Fluorination of Some Fluorine-Containing Oxo Esters by Sulfur Tetrafluoride", *Journal of Fluorine Chemistry*, 1995, 74(2), pp. 259-260.

Feiring, Andrew E. et al., Reaction of Perfluoroalkylethylens With Nucleophiles, *Journal of Fluorine Chemistry*, 1984, 24(1), pp. 125-132.

International Search Report from corresponding PCT/JP2009/050745 dated Apr. 14, 2009, 4 pages.

International Preliminary Report on Patentability and Written Opinion of the International Searching Authority from corresponding PCT application No. PCT/JP2009/050745 dated Sep. 10, 2010, 6 pgs.

* cited by examiner

*Primary Examiner* — Nicole M Buie-Hatcher
(74) *Attorney, Agent, or Firm* — Brinks Hofer Gilson & Lione

(57) ABSTRACT

Disclosed is (1) a mixture of fluoroalkyl alcohol-unsaturated carboxylic acid derivatives represented by the general formulae: $CF_3(CF_2)_n(CH=CF)_a(CF_2CF_2)_b(CH_2CH_2)_c OCOCR=CH_2$ and $CF_3(CF_2)_{n-1}(CF=CH)_a CF_2(CF_2CF_2)_b (CH_2CH_2)_c OCOCR=CH_2$, wherein R is a hydrogen atom or a methyl group, n is an integer of 1 to 5, a is an integer of 1 to 4, b is an integer of 0 to 3, and c is an integer of 1 to 3; (2) a fluorine-containing polymer containing the mixture as a polymerization unit; and (3) a water- and oil-repellent comprising the fluorine-containing polymer as an active ingredient. The fluoroalkyl alcohol-unsaturated carboxylic acid derivatives are produced by an esterification reaction of a mixture of fluoroalkyl alcohols represented by the general formulae: $CF_3(CF_2)_n(CH=CF)_a(CF_2CF_2)_b(CH_2CH_2)_c OH$ and $CF_3 (CF_2)_{n-1}(CF=CH)_a CF_2(CF_2CF_2)_b, (CH_2CH_2)_c OH$, with acrylic acid or methacrylic acid.

12 Claims, No Drawings

MIXTURE OF FLUOROALKYL ALCOHOL-UNSATURATED CARBOXYLIC ACID DERIVATIVES, POLYMER OF THE MIXTURE, AND WATER-AND OIL-REPELLENT CONTAINING THE POLYMER AS ACTIVE INGREDIENT

RELATED APPLICATION

This application is a 35 U.S.C. §371 national phase filing of International Patent Application No. PCT/JP2009/050745, filed Jan. 20, 2009, through which and to which priority is claimed under 35 U.S.C. §119 to Japanese Patent Application Nos. 2008-013386, filed Jan. 24, 2008, 2008-140903, filed May 29, 2008 and 2008-140904, filed May 29, 2008.

TECHNICAL FIELD

The present invention relates to a mixture of fluoroalkyl alcohol-unsaturated carboxylic acid derivatives, a polymer of the mixture, and a water- and oil-repellent containing the polymer as an active ingredient. More specifically, the present invention relates to a mixture of fluoroalkyl alcohol-unsaturated carboxylic acid derivatives containing a perfluoroalkyl group having six or less carbon atoms, which is expected to have low bioaccumulation potential, a polymer of the mixture, and a water- and oil-repellent containing the polymer as an active ingredient.

BACKGROUND ART

Acrylic acid derivatives of perfluoroalkyl alcohol (e.g., $CF_3(CF_2)_7CH_2CH_2OCOCH=CH_2$) are used in large amounts as monomers for synthesizing fluorine-containing copolymers that constitute water- and oil-repellent for textile. Moreover, perfluoroalkyl alcohols serving as acrylated precursors of the acrylic acid derivatives are widely used as surfactants, etc. Thus, the acrylic acid derivatives containing a perfluoroalkyl group having eight or more carbon atoms are used in large amounts as starting materials of water- and oil-repellents, antifouling agents, surfactants, etc., for textile application.

[Patent Document 1] JP-B-63-22237

However, it has been recently reported that perfluorooctanoic acid having eight carbon atoms or perfluorocarboxylic acids having more than eight carbon atoms have adverse effect on the environment, because they are hardly degradability and having high bioaccumulation potential, and may exhibit toxicity to organisms. Among these compounds, those containing a perfluoroalkyl group having eight or more carbon atoms are suggested to be possibly converted to perfluorooctanoic acid or perfluorocarboxylic acids having more than eight carbon atoms by biodegradation or chemical degradation in the environment, and there is concern that it will be difficult to produce and use those compounds for the future. The same applies to telomer compounds. However, compounds containing a perfluoroalkyl group having six or less carbon atoms are said to have low bioaccumulation potential.

According to Patent Document 2, in a surface treatment film of a water- and oil-repellent-treated substrate, the expression of water- and oil-repellency of perfluoroalkyl (meth) acrylate is attributable to the orientation of a perfluoroalkyl group (Rf group) on a treated film, and in order to realize the orientation of the Rf group, the presence of a melting point attributable to fine crystals derived from the Rf group having eight or more carbon atoms is required. For this reason, perfluoroalkyl (meth)acrylate having eight or more carbon atoms is conventionally used; and the water- and oil-repellent performance can be developed by using perfluoroalkyl (meth) acrylate having seven or more carbon atoms in combination with a monomer having an isocyanate group as a crosslinkable group. However, the water- and oil-repellent performance was insufficient when no isocyanate group-containing monomer was used.

[Patent Document 2] WO 2004/035708

DISCLOSURE OF THE INVENTION

[Problems to be Solved by the Invention]

An object of the present invention is to provide:

(1) a mixture of fluoroalkyl alcohol-(meth)acrylic acid derivatives that are compounds having a perfluoroalkyl group containing six or less carbon atoms, which is expected to have low bioaccumulation potential, and forming a CH=CF group vulnerable to biodegradation (biochemical degradation by microorganisms) or chemical degradation (degradation by acids, bases, active oxygen, ozone, etc., in the environment) in the fluoroalkyl group, and that can be effectively used as starting material monomers of water- and oil-repellents, etc.;

(2) a fluorine-containing polymer containing the mixture as a polymerization unit; and (3) a water- and oil-repellent containing the polymer as an active ingredient.

[Means for Solving the Problems]

The object of the present invention can be attained by:

(1) a mixture of fluoroalkyl alcohol-unsaturated carboxylic acid derivatives represented by the general formulae:

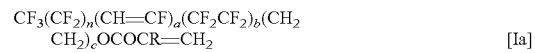  [Ia]

and

  [Ib]

wherein R is a hydrogen atom or a methyl group, n is an integer of 1 to 5, a is an integer of 1 to 4, b is an integer of 0 to 3, and c is an integer of 1 to 3;

(2) a fluorine-containing polymer containing the mixture as a polymerization unit; and (3) a water- and oil-repellent comprising the fluorine-containing polymer as an active ingredient.

The above fluoroalkyl alcohol-unsaturated carboxylic acid derivatives are produced by an esterification reaction of a mixture of fluoroalkyl alcohols represented the general formulae:

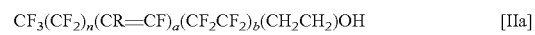  [IIa]

and

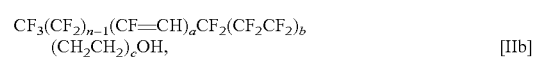  [IIb]

with acrylic acid or methacrylic acid.

[Effect of the Invention]

In the mixture of fluoroalkyl alcohol-unsaturated carboxylic acid derivatives of the present invention, the $CH_2CF_2$ group derived from vinylidene fluoride in the molecule easily undergoes HF-elimination to form a double bond, which is vulnerable to degradation as a result of ozone decomposition; therefore, the perfluoroalkyl group can be decomposed into a group having six or less carbon atoms, which is expected to have low bioaccumulation potential. Accordingly, the fluorine-containing polymer that contains the mixture of fluoroalkyl alcohol-(meth)acrylic acid derivatives as a polymerization unit has —CH=CF— in the fluoroalkyl group, thereby having a structure that does not contain a perfluoroalkyl group having a continuous chain of eight or more carbon atoms. Due to this structure, the polymer is not converted to a perfluorooctanoic acid or a perfluorocarboxylic acids having more than eight carbon atoms in the environment.

The present fluorine-containing polymer can be suitably used as an active ingredient of water- and oil-repellents, as with conventional fluorine-containing polymers. The fluorine-containing polymer containing the mixture of fluoroalkyl alcohol-(meth)acrylic acid derivatives as a polymerization unit has excellent effects, as shown in Examples and Reference Examples, described later. That is, the present polymer has a static contact angle equivalent to that of a conventionally used homopolymer polymerized with perfluorooctylethyl acrylate; and when prepared as an aqueous dispersion, the polymer exhibits water- and oil-repellency equivalent to that of such a homopolymer.

BEST MODE FOR CARRYING OUT THE INVENTION

The mixture of fluoroalkyl alcohol unsaturated-carboxylic-acid derivatives used as the monomer of the fluorine-containing polymer are represented by the general formulae:

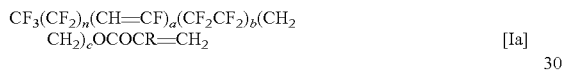

[Ia]

and

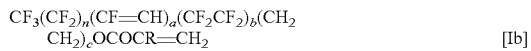

[Ib]

wherein R is a hydrogen atom or a methyl group, n is an integer of 1 to 5, a is an integer of 1 to 4, b is an integer of 0 to 3, and c is an integer of 1 to 3; is produced by an esterification reaction of a mixture of fluoroalkyl alcohols represented by the general formulae:

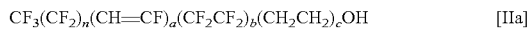

[IIa]

and

[IIb], with acrylic acid or methacrylic acid.

The mixture of fluoroalkyl alcohols [IIa] and [IIb] to be esterified with acrylic acid or methacrylic acid is produced by the reaction of a fluoroalkyl iodide represented by the general formula:

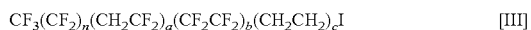

[III]

with N-methylformamide, followed by hydrolysis in the presence of a basic compound.

The fluoroalkyl iodide of the formula:

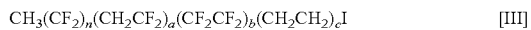

[III]

is produced by the addition reaction of a terminally iodized compound represented by the general formula:

[A]

with ethylene. The ethylene addition reaction is carried out in such a manner that Compound [A] is subjected to an addition reaction with pressurized ethylene in the presence of a peroxide initiator. The number of addition is 1 or more, and preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or less. As a peroxide initiator, tert-butyl peroxide, di(tert-butylcyclohexyl)peroxydicarbonate, dicetyl peroxydicarbonate, or the like may be used at a ratio of about 1 to 5 mol % based on the amount of Compound [A].

Specifically, Compound [A] is represented by the general formula:

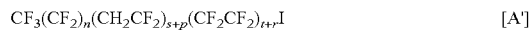

[A']

p: the number of vinylidene fluoride skeletons added by reaction r: the number of tetrafluoroethylene skeletons added by reaction s+p: the same as "a" defined above (1 to 4, preferably 1 to 2)

t+r: the same as "b" defined above (0 to 3, preferably 1 to 2)

More specifically, Compound [A] can be produced by any of the following methods.

(1) A perfluoroalkyl iodide represented by the general formula:

$CF_3(CF_2)_nI$ [B-1], wherein n is an integer of 1 to 5, is reacted with vinylidene fluoride in the presence of a peroxide initiator to produce a terminally iodized polyfluoroalkane oligomer represented by the general formula:

[A-1], wherein n is as defined above, and p is an integer of 1 to 4, indicating the number of vinylidene fluoride skeletons added by reaction.

(2) A terminally iodized polyfluoroalkane represented by the general formula:

[B-2], wherein n is an integer of 1 to 5, s is an integer of 1 to 4, indicating the number of vinylidene fluoride skeletons in the starting material, and t is an integer of 0 to 2, indicating the number of tetrafluoroethylene skeletons in the starting material; is reacted with tetrafluoroethylene in the presence of a peroxide initiator to produce a terminally iodized polyfluoroalkane oligomer represented by the general formula:

[A-2], wherein n, s, and t are as defined above, and r is an integer of 1 to 3, indicating the number of tetrafluoroethylene skeletons added by reaction.

(3) A terminally iodized polyfluoroalkane represented by the general formula:

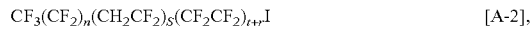

[B-3], wherein n is an integer of 1 to 5, s is an integer of 1 to 3, indicating the number of vinylidene fluoride skeletons in the starting material, and t is an integer of 1 to 3, indicating the number of tetrafluoroethylene skeletons in the starting material; is reacted with vinylidene fluoride in the presence of a peroxide initiator to produce a terminally iodized polyfluoroalkane oligomer represented by the general formula:

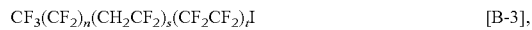

[A-3], wherein n, s, and t are as defined above, and p is an integer of 1 to 3, indicating the number of vinylidene fluoride skeletons added by reaction.

Specific examples of terminally iodized polyfluoroalkanes usable in the present invention include the following compounds:

$CF_3(CF_2)(CH_2CF_2)I$ $CF_3(CF_2)(CH_2CF_2)_2I$ $CF_3(CF_2)_2(CH_2CF_2)I$ $CF_3(CF_2)_2(CH_2CF_2)_2I$ $CF_3(CF_2)_3(CH_2CF_2)I$ $CF_3(CF_2)_3(CH_2CF_2)_2I$ $CF_3(CF_2)(CH_2CF_2)(CF_2CF_2)I$ $CF_3(CF_2)(CH_2CF_2)(CF_2CF_2)_2I$ $CF_3(CF_2)_2(CH_2CF_2)(CF_2CF_2)I$ $CF_3(CF_2)_2(CH_2CF_2)(CF_2CF_2)_2I$ $CF_3(CF_2)_3(CH_2CF_2)_2(CF_2CF_2)I$ $CF_3(CF_2)_3(CH_2CF_2)_2(CF_2CF_2)_2I$

The oligomerization reaction of the perfluoroalkyl iodide or terminally iodized polyfluoroalkane of the formula [B-1], [B-2], or [B-3] with vinylidene fluoride or tetrafluoroethylene is carried out in the presence of a peroxide initiator, such as di(tert-butylcyclohexyl)peroxydicarbonate, dicetyl peroxydicarbonate, etc. A peroxide initiator is used at a ratio of about 0.1 to 0.5 mol % based on the amount of Compound [B-1], [B-2], or [B-3], and p and r indicate the increased degree of oligomerization of vinylidene fluoride or tetrafluoroethylene, respectively. Although the reaction temperature depends on the degeneration temperature of the initiator used, the reaction can be carried out at 80° C. or less by using a peroxide initiator that decomposes at a low temperature.

The fluoroalkyl iodide [III] is reacted with N-methylformamide, followed by hydrolysis in the presence of a basic compound, thereby forming a mixture of fluoroalkyl alcohols represented by the general formulae:

$CF_3(CF_2)_n(CH=CF)_a(CF_2CF_2)_b(CH_2CH_2)_cOH$ [IIa]

and $CF_3(CF_2)_{n-1}(CF=CH)_aCF_2(CF_2CF_2)_b(CH_2CH_2)_cOH$ [IIb]

Here, the mixture of Compounds [IIa] and [IIb] is formed because in the HF-elimination reaction, the elimination of the H atom of the methylene chain $CH_2$ and the F atom of either one of the fluoromethylene chains $CF_2$ bonding back and forth to the $CH_2$ occurs equally in the anteroposterior position. Moreover, since the HF-elimination reactions are equivalent, the proportion of the produced Compounds [IIa] and [IIb] is approximately 1:1. Although Compounds [IIa] and [IIb] cannot be separately identified because they are very similar constitutional isomers, a mixture of these compounds can be directly used as a synthetic starting material of other substances because they have equivalent reactivity.

This reaction is carried out by reacting the fluoroalkyl iodide [III] with N-methylformamide in an amount of about 5 to 20 times by mole, and preferably about 10 to 15 times by mole, based on the amount of fluoroalkyl iodide [II] at about 140 to 160° C. for about 7 to 10 hours, followed by a reaction with a basic compound such as sodium hydroxide, potassium hydroxide, etc. at about 85 to 95° C. for about 7 to 10 hours.

The obtained mixture of fluoroalkyl alcohols [IIa] and [IIb] can be subjected to an esterification reaction with acrylic acid or methacrylic acid. The esterification reaction is conducted as follows: An aromatic hydrocarbon solvent such as toluene, benzene, etc., a catalyst such as p-toluenesulfonic acid, etc., and hydroquinone, which is used as a polymerization inhibitor, are added to the fluoroalkyl alcohol mixture, followed by heating at about 90 to 100° C. Then, about 1 to 2 times by mole of acrylic acid or methacrylic acid is added, and the resultant mixture is heated at about 110 to 120° C. for about 2 to 5 hours, followed by dehydration and esterification reaction, thereby providing a mixture of acrylic acid or methacrylic acid derivatives [Ia] and [Ib].

The thus-produced mixture of fluoroalkyl alcohol-(meth) acrylic acid derivative monomers of the formulae:

$CF_3(CF_2)_n(CH=CF)_a(CF_2CF_2)_b(CH_2CH_2)_cOCOCR=CH_2$ [Ia]

and $CF_3(CF_2)_{n-1}(CF=CH)_aCF_2(CF_2CF_2)_b(CH_2CH_2)_cOCOCR=CH_2$ [Ib]

can be subjected to a polymerization reaction in a fluorine-containing organic solvent such as 1,4-bis(trifluoromethyl)benzene, 1,1,1,2,2-pentafluoro-3,3-dichloropropane, 1,1,2,2,3-pentafluoro-1,3-dichloropropane, etc. in the presence of an organic peroxide such as bis(4-tert-butylcyclohexyl)peroxydicarbonate, di-n-propylperoxydicarbonate, diisopropylperoxydicarbonate, etc. that is used at a ratio of about 1 to 4 wt. %, preferably about 1 to 2 wt. %, based on the monomers, at about 40 to 50° C. for about 15 to 25 hours, thereby forming a polymer containing only the mixture of fluoroalkyl alcohol-(meth)acrylic acid derivative monomers as a polymerizable monomer.

It is also possible to copolymerize the mixture with other fluorine-containing polymerizable monomers and/or fluorine-free polymerizable monomers. When other fluorine-containing polymerizable monomers are used, the number of carbons in the polyfluoroalkyl group, preferably perfluoroalkyl group, of the monomers must be 1 to 6, preferably 2 to 4.

As other fluorine-containing polymerizable monomers, those represented by the following general formula are preferably used.

$CH_2=CRCOOR_1(NR_2SO_2)_mRf$

R: a hydrogen atom or a methyl group
$R_1$: a divalent organic group having 1 to 4 carbon atoms
$R_2$: a lower alkyl group having 1 to 5 carbon atoms
Rf: a polyfluoroalkyl group, preferably perfluoroalkyl group, having carbon atoms of 1 to 6, preferably 2 to 4
m: 0 or 1

For example, the following polyfluoroalkyl group-containing (meth)acrylate monomers are used, with the proviso that the number of carbon atoms n in the terminal polyfluoroalkyl group is 1 to 6, and that when $R_1$ is a polyfluoroalkylene group, the total number of carbon atoms in the polyfluoroalkylene group and terminal polyfluoroalkyl group is 1 to 6.

$CH_2=CHCOOC_2C_nF_{2n}H$ $CH_2C(CH_3)COOCH_2C_nF_{2n}H$ $CH_2=CHCOOCH_2C_nF_{2n+1}$ $CH_2=C(CH_3)COOCH_2C_nF_{2n+1}$ $CH_2=CHCOOC_2H_4C_nF_{2n+1}$ $CH_2=C(CH_3)COOC_2H_4C_nF_{2n+1}$ $CH_2=CHCOOC_3H_6C_nF_{2n+1}$ $CH_2=C(CH_3)COOC_3H_6C_nF_{2n+1}$ $CH_2=CHCOOC_4H_8C_nF_{2n+1}$ $CH_2=C(CH_3)COOC_4H_8C_nF_{2n+1}$ $CH_2=CHCOOC_2H_4N(CH_3)SO_2C_nF_{2n+1}$ $CH_2=C(CH_3)COOC_2H_4N(CH_3)SO_2C_nF_{2n+1}$ $CH_2=CHCOOC_2H_4N(C_2H_5)SO_2C_nF_{2n+1}$ $CH_2=C(CH_3)COOC_2H_4N(C_2H_5)SO_2C_nF_{2n+1}$ $CH_2=CHCOOC_2H_4N(C_3H_7)SO_2C_nF_{2n+1}$ $CH_2=C(CH_3)COOC_2H_4N(C_3H_7)SO_2C_nF_{2n+1}$ $CH_2=CHCOOC_2H_4C_nF_{2n}CF(CF_3)_2$ $CH_2=C(CH_3)COOC_2H_4C_nF_{2n}CF(CF_3)_2$

Moreover, examples of fluorine-free polymerizable monomers include acrylic acid or methacrylic acid esters esterified with alkyl groups such as methyl, ethyl, propyl, isopropyl, n-butyl, n-hexyl, 2-ethylhexyl, n-octyl, lauryl and stearyl, cycloalkyl groups such as cyclohexyl, aralkyl groups such as benzyl, or alkoxyalkyl groups such as methoxymethyl, 2-methoxyethyl, 2-ethoxyethyl, 2-butoxyethyl, and 3-ethoxypropyl; monoalkyl or dialkyl esters, such as monomethyl, dimethyl, monoethyl, diethyl, monopropyl, dipropyl, monobutyl, dibutyl, mono-2-ethylhexyl, di-2-ethylhexyl, monooctyl and dioctyl esters, of fumaric acid or maleic acid; vinyl esters, such as vinyl acetate and vinyl caprylate; preferably alkyl (meth)acrylates containing a long-chain alkyl group having eight or more carbon atoms (e.g., 2-ethylhexyl, n-octyl, lauryl, and stearyl), and (meth)acrylic acid esters esterified with cycloalkyl groups such as cyclohexyl, or aralkyl groups such as benzyl; and more preferably a combination of acrylic acid esters esterified with alkyl groups such as 2-ethylhexyl and stearyl, with (meth)acrylic acid esters esterified with aralkyl groups such as benzyl, in terms of the balance of water-repellency and oil-repellency.

In a copolymer of such other polymerizable monomers, it is preferable to copolymerize the mixture of fluoroalkyl alcohol-(meth)acrylic acid derivatives as a polymerization unit at a ratio of about 5 wt. % or more, preferably about 10 to 60 wt. %, more preferably about 10 to 35 wt. % in the copolymer, in terms of the development of water- and oil-repellency. Needless to say, polymers comprising only the mixture of fluoroalkyl alcohol-(meth)acrylic acid derivatives as a polymerizable monomer exhibit water- and oil-repellency; however, copolymers of the mixture with other comonomers are advantageous in terms of cost. Particularly, it is preferable in terms of both water- and oil-repellency and cost to copolymerize the polyfluoroalkyl group-containing (meth)acrylate monomer, which per se exhibits water- and oil-repellency, as a polymerization unit at a ratio of about 10 wt. % or more, preferably about 10 to 60 wt. %, in the copolymer.

The copolymer can be copolymerized with other copolymerizable monomers in an amount that does not impair the properties, for example, at a ratio of 30 wt. % or less in the copolymer. Examples of such copolymerizable monomers include styrene, vinyl toluene, α-methyl styrene, vinyl naphthalene, acrylonitrile, methacrylonitrile, acetone acrylamide, isoprene, pentadiene, butadiene, 2-hydroxyethyl acrylate, 4-hydroxybutyl acrylate, 2-hydroxy-3-chloropropyl (meth)acrylate, polyethyleneglycol mono(meth)acrylate, polypropyleneglycol mono(meth)acrylate, vinylidene chloride, vinyl fluoride, vinylidene fluoride, hydroxyethyl vinyl ether, and hydroxybutyl vinyl ether.

If necessary, the copolymer can be copolymerized with polyfunctional monomers or oligomers at 30 wt. % or less in the copolymer. Examples of such polyfunctional monomers or oligomers include ethyleneglycol di(meth)acrylate, propyleneglycol di(meth)acrylate, 1,4-butanediol di(meth)acrylate, 1,6-hexanediol di(meth)acrylate, 1,9-nonanediol di(meth)acrylate, neopentylglycol di(meth)acrylate, tetraethyleneglycol di(meth)acrylate, tripropyleneglycol di(meth)acrylate, polypropyleneglycol di(meth)acrylate, bisphenol A.ethylene oxide adduct diacrylate, dimethylol tricyclodecane diacrylate, glycerin methacrylate acrylate, 3-acryloyloxyglycerine monomethacrylate, and the like.

In this case, crosslinkable group-containing monomers, such as (meth)acrylamide, N-methylol (meth)acrylamide, N-methoxymethyl acrylamide, N-butoxymethyl acrylamide, glycidyl (meth)acrylate, can be added together with a radical polymerization initiator and copolymerized at a ratio of about 10 wt. % or less, preferably about 0.5 to 7 wt. %, in the copolymer. When these crosslinkable group-containing monomers are further copolymerized, they are crosslinked with hydroxyl groups on the fiber surface or self-crosslinked to enhance the durability of water- and oil-repellents.

The method for producing the fluorine-containing copolymer is not particularly limited; for example, a solution polymerization method using an organic solvent, a suspension polymerization method or an emulsion polymerization method using water as a dispersion medium and containing a nonionic and/or cationic surfactant, or other method can be used. Polymer solutions obtained by a solution polymerization method are used as water- and oil-repellents after being diluted with a fluorine-containing organic solvent, such as 1,4-bis(trifluoromethyl)benzene, 1,3-bis(trifluoromethyl)benzene, etc. to a solid matter content of about 0.01 to 30 wt. %, preferably about 0.05 to 5 wt. %. Aqueous dispersions of copolymers obtained by a suspension polymerization method or emulsion polymerization method are used as water- and oil-repellents directly or after being diluted with water to a solid matter content of about 0.1 to 10 wt. %. In the case of using a suspension polymerization method or emulsion polymerization method, a flocculating agent is added to a polymerization reaction solution to coagulate a polymer, and the polymer only containing the mixture of fluoroalkyl alcohol (meth)acrylic acid derivatives as a polymerizable monomer separated by washing with water or an organic solvent, or a copolymer of the mixture with other polymerizable monomer, is dissolved in a fluorine-containing organic solvent or dispersed in water, thereby preparing a water- and oil-repellent comprising the organic solvent solution or aqueous dispersion thereof.

The thus-obtained polymer containing only the mixture of fluoroalkyl alcohol (meth)acrylic acid derivatives as a polymerizable monomer, or copolymer of the mixture with other polymerizable monomer is separated by evaporation to dryness and purified by washing with a solvent, etc. The weight average molecular weight Mw of the obtained polymer only containing the mixture of fluoroalkyl alcohol (meth)acrylic acid derivatives as a polymerizable monomer, or copolymer of the mixture with other polymerizable monomer is measured by high-speed liquid chromatography, and the value is 2,000 to 20,000,000. The weight average molecular weight Mw was measured by GPC using Shodex GPC KD806M+ KD-802+KD-G at a temperature of 40° C. under the condition where the elution rate of 10 mM THF (i.e., eluate) was 1 ml/min. The detector used was a differential refractive index detector, and the analysis was conducted using Labchat 180 (manufactured by SIC) in terms of polystyrene.

Although an aqueous dispersion of the polymer only containing the mixture of fluoroalkyl alcohol (meth)acrylic acid derivatives as a polymerizable monomer, or copolymer of the mixture with other polymerizable monomer, preferably an aqueous dispersion containing a surfactant and a water-soluble organic solvent in an amount of 20 wt. % or less or a fluorine-containing organic solvent solution can be solely used as a water- and oil-repellent; if necessary, crosslinking agents such as melamine resins, urea resins, etc., other than blocked isocyanates; polymer extenders, other water-repellents such as silicon resin or oil, wax, etc., insecticides, antistatic agents, dye stabilizers, anti-wrinkle agents, stain blockers, and other additives that are necessary for water- and oil-repellent application may be added.

The water- and oil-repellents obtained in this manner can effectively be applied to paper, film, fiber, cloth, fabric, carpet, or textile products made of filament, fiber, yarn, etc. As the application method of the water- and oil-repellents, coating, immersing, spraying, padding, roll-coating, or a combination of these methods are generally used. For example, the water- and oil-repellents are used as a pad bath by adjusting the solid matter content of the bath to about 0.1 to 10 wt. %. A material to be processed is padded in the pad bath, and the excessive solution is removed squeeze rolls, followed by drying, so that the amount of the polymer adhered to the material is about 0.01 to 10 wt. %. Subsequently, drying is generally carried out at a temperature of about 100 to 200° C. for about 1 minute to about 2 hours, although depending on the kind of material to be processed. Thus, the water- and oil-repellent treatment is completed.

EXAMPLES

The following describes the present invention with reference to examples.

Reference Example 1

(1) A compound of the formula: $CF_3(CF_2)_3(CH_2CF_2)(CF_2CF_2)_2I$ (99GC %) (603g; 0.99 mol) and 7g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 41 g (1.45 mol) of ethylene was introduced over about 3 hours. The content was collected at an internal temperature of 50° C. or less, thereby obtaining 637 g of compound of the formula: $CF_3(CF_2)_3(CH_2CF_2)(CF_2CF_2)_2(CH_2CH_2)I$ (98GC %) (yield: 98.8%).

(2) The compound of the formula: $CF_3(CF_2)_3(CH_2CF_2)(CF_2CF_2)_2(CH_2CH_2)I$ (98GC %) (150 g; 0.23 mol) obtained above (1) and 170 g (2.88 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 133 g of lower layer of the mixture was mixed with 140 g of a 10 wt. % NaOH aqueous solution, followed by reaction under stirring at 90° C. for 8 hours. After the reaction mixture was allowed to stand, 124 g of reaction product (66.4GC %), which was light-yellow, transparent liquid at ambient temperature, was obtained as the lower layer of the mixture (yield: 70.5%).

The reaction product was subjected to distillation under reduced pressure under conditions where the internal pressure was 0.2 kPa, the internal temperature was 109 to 123° C., and the overhead temperature was 86 to 87° C. Thus, 30 g of purified reaction product (97.4GC %) was obtained (distillation yield: 35.6%). The results of $^1$H-NMR and $^{19}$F-NMR confirmed that this purified reaction product was a mixture of compounds represented by the following formulae:

$CF_3(CF_2)_3(CH{=}CF)(CF_2CF_2)_2(CH_2CH_2)OH$ $CF_3(CF_2)_2(CF{=}CH)CF_2(CF_2CF_2)_2(CH_2CH_2)OH$ $^1$H-NMR (CDCl$_3$, TMS):
δ5.71-5.92 (C$\underline{H}$=CF, CF=C$\underline{H}$)
2.28-2.45 (C$\underline{H_2}$CH$_2$)
3.97 (CH$_2$C$\underline{H_2}$)
2.28-2.45 (O$\underline{H}$)
$^{19}$F-NMR (C$\overline{D}$Cl$_3$, C$_6$F$_6$):
ppm −82.13 to −81.77 (CF$_3$)
−128.22 to −126.84 (C$\overline{F_3}$CF$_2$CF$_2$)
−125.52 to −124.83 (CF$_3$C$\overline{F_2}$CF$_2$)
−111.22 to −109.58 (CF$_2$CH=C$\overline{F}$, CF=CHCF$_2$)
−120.76 to −119.73 (C$\overline{F_2}$CF$_2$CF$_2$C$\overline{F_2}$CH$_2$)
−123.69 to −122.27 (C$\overline{F_2}$CF$_2$CF$_2$CF$_2$CH$_2$)
−114.44 (CF$_2$CF$_2$CF$_2$CF$_2$C$\overline{H_2}$)
−124.73 (CF$_2$CF$_2$C$\overline{F_2}$C$\underline{F_2}$CH$_2$)

Example 1

The mixture of compounds (97.4GC %) obtained in Reference Example 1 (2) (30.0 g; 0.06 mol), 21 g of toluene, 6 g of p-toluenesulfonic acid, and 0.3 g of hydroquinone were charged in a four-necked 100-ml flask equipped with a condenser, thermometer, and stirrer. After the internal temperature was raised to 100° C., 5 g (0.07 mol) of acrylic acid was added, and the mixture was stirred for reaction at an internal temperature of 115° C. for 4 hours. After the completion of the reaction, the toluene was removed by an evaporator from 61 g of the reaction mixture solution obtained by cooling, and 42 g of residue was washed with tap water. Thus, 34 g of reaction product (86.9GC %), which was light-yellow, transparent liquid at ambient temperature, was obtained (yield: 84.1%).

The reaction product was subjected to distillation under reduced pressure under conditions where the internal pressure was 0.1 kPa, the internal temperature was 128 to 133° C., and the overhead temperature was 64 to 72° C. Thus, 23 g of purified reaction product (98.0GC %) was obtained (distillation yield: 77.7%). The results of $^1$H-NMR and $^{19}$F-NMR confirmed that this purified reaction product was a mixture of compounds represented by the following formulae:

$CF_3(CF_2)_3(CH{=}CF)(CF_2CF_2)_2(CH_2CH_2)$
    $OCOCH{=}CH_2$ $CF_3(CF_2)_2(CF{=}CH)CF_2(CF_2CF_2)_2(CH_2CH_2)$
    $OCOCH{=}CH_2$ $^1$H-NMR (CDCl$_3$, TMS):
δ5.73-5.97 (C$\underline{H}$=CF, CF=C$\underline{H}$)
2.48 (CH$_2$CH$_2$)
4.46 (C$\underline{H_2}$CH$_2$)
6.14 (C$\underline{H}$=CH$_2$)
6.41, 5.$\overline{7}$3-5.97 (CH=C$\underline{H_2}$)

$^{19}$F-NMR (CDCl$_3$, C$_6$F$_6$):
ppm −82.06 to −81.73 (CF$_3$)
−128.22 to −126.84 (CF$_3$CF$_2$CF$_2$)
−125.52 to −124.81 (CF$_3$CF$_2$CF$_2$)
−111.22 to −109.58 (CF$_2$CH=CF, CF=CHCF$_2$)
−120.76 to −119.73 (CF$_2$CF$_2$CF$_2$CF$_2$CH$_2$)
−123.69 to −122.27 (CF$_2$CF$_2$CF$_2$CF$_2$CH$_2$)
−114.54 (CF$_2$CF$_2$CF$_2$CF$_2$CH$_2$)
−124.56 (CF$_2$CF$_2$CF$_2$CF$_2$CH$_2$)

Reference Example 2

(1) A compound of the formula: CF$_3$(CF$_2$)$_3$(CH$_2$CF$_2$)(CF$_2$CF$_2$)I (99.3GC %) (609 g; 1.19 mol) and 6 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 640 g of compound of the formula: CF$_3$(CF$_2$)$_3$(CH$_2$CF$_2$)(CF$_2$CF$_2$)(CH$_2$CH$_2$)I (97.4GC %) (yield: 97.3%).

(2) The compound of the formula: CF$_3$(CF$_2$)$_3$(CH$_2$CF$_2$)(CF$_2$CF$_2$)(CH$_2$CH$_2$)I (97.4GC %) (153 g; 0.28 mol) obtained above (1) and 207 g (3.51 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 135 g of lower layer of the mixture was mixed with 140 g of a 10 wt. % NaOH aqueous solution, followed by reaction under stirring at 90° C. for 8 hours. After the reaction mixture was allowed to stand, 132 g of reaction product (65.3GC %), which was light-yellow, transparent liquid at ambient temperature, was obtained as the lower layer of the mixture (yield: 75.4%).

The reaction product was subjected to distillation under reduced pressure under conditions where the internal pressure was 0.2 kPa, the internal temperature was 103 to 108° C., and the overhead temperature was 84 to 85° C. Thus, 38 g of purified reaction product (97.8GC %) was obtained (distillation yield: 42.8%). The results of $^1$H-NMR and $^{19}$F-NMR confirmed that this purified reaction product was a mixture of compounds represented by the following formulae:

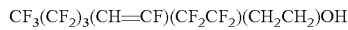

CF$_3$(CF$_2$)$_3$(CH=CF)(CF$_2$CF$_2$)(CH$_2$CH$_2$)OH

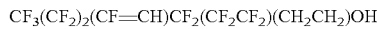

CF$_3$(CF$_2$)$_2$(CF=CH)CF$_2$(CF$_2$CF$_2$)(CH$_2$CH$_2$)OH $^1$H-NMR (CDCl$_3$, TMS):
δ5.75-5.88 (CH=CF, CF=CH)
2.35 (CH$_2$CH$_2$)
3.93 (CH$_2$CH$_2$)
3.07-3.28 (OH)
$^{19}$F-NMR (CDCl$_3$, C$_6$F$_6$):
ppm −82.0 to −81.6 (CF$_3$)
−128.0 to −126.6 (CF$_3$CF$_2$CF$_2$)
−125.3 to −124.6 (CF$_3$CF$_2$CF$_2$)
−111.1 to −108.8 (CF$_2$CH=CF, CF=CHCF$_2$)
−126.6 (CF$_2$CF$_2$CH$_2$)
−113.2 (CF$_2$CF$_2$CH$_2$)

Example 2

The mixture of compounds (97.8GC %) obtained in Reference Example 2 (2) (37 g; 0.09 mol), 23 g of toluene, 7 g of p-toluenesulfonic acid, and 0.4 g of hydroquinone were charged in a four-necked 100-ml flask equipped with a condenser, thermometer, and stirrer. After the internal temperature was raised to 100° C., 8 g (0.11 mol) of acrylic acid was added, and the mixture was stirred for reaction at an internal temperature of 115° C. for 4 hours. After the completion of the reaction, the toluene was removed by an evaporator from 74 g of the reaction mixture solution obtained by cooling, and 53 g of residue was washed with tap water. Thus, 42 g of reaction product (88.1GC %), which was light-yellow, transparent liquid at ambient temperature, was obtained (yield: 85.4%).

The reaction product was subjected to distillation under reduced pressure under conditions where the internal pressure was 0.1 kPa, the internal temperature was 124 to 128° C., and the overhead temperature was 63 to 68° C. Thus, 30 g of purified reaction product (99.2GC %) was obtained (distillation yield: 79.2%). The results of $^1$H-NMR and $^{19}$F-NMR confirmed that this purified reaction product was a mixture of compounds represented by the following formulae:

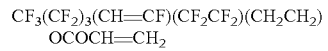

CF$_3$(CF$_2$)$_3$(CH=CF)(CF$_2$CF$_2$)(CH$_2$CH$_2$)
   OCOCH=CH$_2$

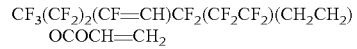

CF$_3$(CF$_2$)$_2$(CF=CH)CF$_2$(CF$_2$CF$_2$)(CH$_2$CH$_2$)
   OCOCH=CH$_2$ $^1$H-NMR (CDCl$_3$, TMS):
δ5.75-5.88 (CH=CF, CF=CH)
2.52 (CH$_2$CH$_2$)
4.46 (CH$_2$CH$_2$)
6.13 (CH=CH$_2$)
6.41, 5.89 (CH=CH$_2$)
$^{19}$F-NMR (CDCl$_3$, C$_6$F$_6$):
ppm −82.0 to −81.7 (CF$_3$)
−127.9 to −126.5 (CF$_3$CF$_2$CF$_2$)
−125.4 to −124.8 (CF$_3$CF$_2$CF$_2$)
−110.9 to −110.2 (CF$_2$CH=CF, CF=CHCF$_2$)
−126.7 (CF$_2$CF$_2$CH$_2$)
−113.7 (CF$_2$CF$_2$CH$_2$)

Reference Example 3

(1) A compound of the formula: CF$_3$CF$_2$(CH$_2$CF$_2$)(CF$_2$CF$_2$)$_3$I (98.7GC %) (605 g: 0.98 mol) and 7 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 43 g (1.53 mol) of ethylene was introduced over about 3 hours. The content was collected at an internal temperature of 50° C. or less, thereby obtaining 630 g of compound of the formula: CF$_3$CF$_2$(CH$_2$CF$_2$)(CF$_2$CF$_2$)$_3$(CH$_2$CH$_2$)I (97.7GC %) 98.5% of). (2) The compound of the formula: CF$_3$CF$_2$(CH$_2$CF$_2$)(CF$_2$CF$_2$)$_3$(CH$_2$CH$_2$)I (97.7GC %) (150 g; 0.23 mol) obtained above (1) and 170 g (2.88 mol) of N-methyl-formamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 132 g of lower layer of the mixture was mixed with 141 g of a 10 wt % NaOH aqueous solution, followed by reaction under stirring at 90° C. for 8 hours. After the reaction mixture was allowed to stand, 126 g of reaction product (66.1GC %), which was light-yellow, transparent liquid at ambient temperature, was obtained as the lower layer of the mixture (yield: 71.4%).

The reaction product was subjected to distillation under reduced pressure under conditions where the internal pressure was 0.2 kPa, the internal temperature was 110 to 123° C., and the overhead temperature was 85 to 87° C. Thus, 31 g of purified reaction product (97.5GC %) was obtained (distillation yield: 35.9%). The results of $^1$H-NMR and $^{19}$F-NMR confirmed that this purified reaction product was a mixture of compounds represented by the following formulae:

$$CF_3CF_2(CH=CF)(CF_2CF_2)_3(CH_2CH_2)OH$$

$$CF_3(CF=CH)CF_2(CF_2CF_2)_3(CH_2CH_2)OH$$

$^1$H-NMR (CDCl$_3$, TMS):
δ5.13-5.84 (C$\underline{H}$=CF, CF=C$\underline{H}$)
2.28-2.45 (C$\underline{H_2}$CH$_2$)
3.97 (CH$_2$C$\underline{H_2}$)
2.27-2.47 (O$\underline{H}$)
$^{19}$F-NMR (CDCl$_3$, C$_6$F$_6$):
ppm −87.1 to −86.7 (CF$_3$)
 −118.1 to −109.7 (C$\underline{F_2}$CH=CF, CF=CHC$\underline{F_2}$)
 −120.8 to −119.6 (C$\underline{F_2}$CF$_2$CF$_2$CF$_2$CF$_2$CH$_2$)
 −120.4 to −119.3 (C$\underline{F_2}$CF$_2$CF$_2$CF$_2$CF$_2$CH$_2$)
 −120.4 to −119.3 (CF$_2$C$\underline{F_2}$CF$_2$CF$_2$CF$_2$CF$_2$CH$_2$)
 −123.4 to −122.1 (CF$_2$CF$_2$C$\underline{F_2}$CF$_2$CF$_2$CF$_2$CH$_2$)
 −124.6 (CF$_2$CF$_2$CF$_2$CF$_2$CF$_2$C$\underline{F_2}$CH$_2$)
 −114.6 (CF$_2$CF$_2$CF$_2$CF$_2$C$\underline{F_2}$CF$_2$CH$_2$)

Example 3

The mixture of compounds (97.5GC %) obtained in Reference Example 3 (2) (30.0 g; 0.06 mol), 21 g of toluene, 6 g of p-toluenesulfonic acid, and 0.3 g of hydroquinone were charged in a four-necked 100-ml flask equipped with a condenser, thermometer, and stirrer. After the internal temperature was raised to 100° C., 5 g (0.07 mol) of acrylic acid was added, and the mixture was stirred for reaction at an internal temperature of 115° C. for 4 hours. After the completion of the reaction, the toluene was removed by an evaporator from 61 g of the reaction mixture solution obtained by cooling, and 42 g of residue was washed with tap water. Thus, 34 g of reaction product (87.3GC %), which was light-yellow, transparent liquid at ambient temperature, was obtained (yield: 84.7%).

The reaction product was subjected to distillation under reduced pressure under conditions where the internal pressure was 0.1 kPa, the internal temperature was 129 to 133° C., and the overhead temperature was 65 to 72° C. Thus, 24 g of purified reaction product (99.3GC %) was obtained (distillation yield: 78.3%). The results of $^1$H-NMR and $^{19}$F-NMR confirmed that this purified reaction product was a mixture of compounds represented by the following formulae:

$$CF_3CF_2(CH=CF)(CF_2CF_2)_3(CH_2CH_2)OCOCH=CH_2$$

$$CF_3(CF=CH)CF_2(CF_2CF_2)_3(CH_2CH_2)OCOCH=CH_2$$

$^1$H-NMR (CDCl$_3$, TMS):
δ5.72-5.85 (C$\underline{H}$=CF, CF=C$\underline{H}$)
2.51 (C$\underline{H_2}$CH$_2$)
4.46 (CH$_2$C$\underline{H_2}$)
6.13 (CH=C$\underline{H}_2$)
6.41, 5.$\overline{89}$ (CH=C$\underline{H}_2$)
$^{19}$F-NMR (CDCl$_3$, $\overline{C_6F_6}$):
ppm −87.0 to −86.7 (CF$_3$)
 −117.6 to −110.4 (C$\underline{F_2}$CH=CF, CF=CHC$\underline{F_2}$)
 −121.7 to −119.9 (C$\underline{F_2}$CF$_2$CF$_2$C$\underline{F_2}$CF$_2$CF$_2$CH$_2$)
 −120.9 to −120.0 (C$\underline{F_2}$CF$_2$CF$_2$CF$_2$CF$_2$CF$_2$CH$_2$)
 −120.9 to −120.0 (CF$_2$C$\underline{F_2}$CF$_2$CF$_2$CF$_2$CF$_2$CH$_2$)
 −123.3 to −122.0 (CF$_2$CF$_2$C$\underline{F_2}$CF$_2$CF$_2$CF$_2$CH$_2$)
 −124.4 (CF$_2$CF$_2$CF$_2$CF$_2$CF$_2$CF$_2$C$\underline{H_2}$)
 −114.5 (CF$_2$CF$_2$CF$_2$CF$_2$C$\underline{F_2}$CF$_2$CH$_2$)

Example 4

The mixture of compounds (97.4GC %) obtained in Reference Example 1 (2) (30.0 g; 0.06 mol), 21 g of toluene, 6 g of p-toluenesulfonic acid, and 0.3 g of hydroquinone were charged in a four-necked 100-ml flask equipped with a condenser, thermometer, and stirrer. After the internal temperature was raised to 100° C., 6 g (0.07 mol) of methacrylic acid was added, and the mixture was stirred for reaction at an internal temperature of 115° C. for 4 hours. After the completion of the reaction, the toluene was removed by an evaporator from 62 g of the reaction mixture solution obtained by cooling, and 42 g of residue was washed with tap water. Thus, 35 g of reaction product (89.4GC %), which was light-yellow, transparent liquid at ambient temperature, was obtained (yield: 94.9%).

The reaction product was subjected to distillation under reduced pressure under conditions where the internal pressure was 0.1 kPa, the internal temperature was 135 to 142° C., and the overhead temperature was 70 to 76° C. Thus, 26.5 g of purified reaction product (99.1GC %) was obtained (distillation yield: 792%). The results of $^1$H-NMR and $^{19}$F-NMR confirmed that this purified reaction product was a mixture of compounds represented by the following formulae:

$$CF_3(CF_2)_3(CH=CF)(CF_2CF_2)_2(CH_2CH_2)OCOC(CH_3)=CH_2$$

$$CF_3(CF_2)_2(CF=CH)CF_2(CF_2CF_2)_2(CH_2CH_2)OCOC(CH_3)=CH_2$$

$^1$H-NMR (CDCl$_3$, TMS):
δ5.75-5.88 (C$\underline{H}$=CF, CF=C$\underline{H}$)
2.51 (C$\underline{H_2}$CH$_2$)
4.45 (C$\underline{H_2}$CH$_2$)
1.94 (C(C$\underline{H_3}$)=CH$_2$)
6.31, 5.61 (C(CH$_3$)=C$\underline{H_2}$)
$^{19}$F-NMR (CDCl$_3$, $\overline{C_6F_6}$):
ppm −82.1 to −81.8 (CF$_3$)
 −127.5 to −126.2 (C$\underline{F_3}$CF$_2$CF$_2$)
 −125.4 to −124.8 (CF$_3$C$\underline{F_2}$CF$_2$)
 −110.8 to −110.5 (CF$_2$CH=$\overline{CF}$, CF=CHCF$_2$)
 −120.7 to −119.8 (C$\underline{F_2}$CF$_2$CF$_2$CF$_2$CH$_2$)
 −123.7 to −122.4 (C$\underline{F_2}$CF$_2$CF$_2$CF$_2$CH$_2$)
 −124.6 (CF$_2$CF$_2$CF$_2$C$\underline{F_2}$CH$_2$)
 −114.6 (CF$_2$CF$_2$C$\underline{F_2}$CF$_2$CH$_2$)

Reference Example 4

(1) A compound of the formula: CF$_3$CF$_2$(CH$_2$CF$_2$)(CF$_2$CF$_2$)$_2$I (99.4GC %) (605 g; 1.18 mol) and 6 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. At an internal temperature of 50° C. or less, the content was collected, thereby obtaining 639 g of compound of the formula: CF$_3$CF$_2$(CH$_2$CF$_2$)(CF$_2$CF$_2$)$_2$(CH$_2$CH$_2$)I (97.3GC %) (yield: 98.0%).

(2) The compound of the formula: CF$_3$CF$_2$(CH$_2$CF$_2$)(CF$_2$CF$_2$)$_2$(CH$_2$CH$_2$)I (97.3GC %) (150 g; 0.27 mol) obtained above (1) and 205 g (3.48 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 134 g of lower layer of the mixture was mixed with 140 g of a 10 wt. % NaOH aqueous solution, followed by reaction under stirring at 90° C. for 8 hours. After the reaction mixture was allowed to stand, 127 g of reaction product (67.1GC %), which was light-yellow transparent liquid at ambient temperature, was obtained as the lower layer of the mixture (yield: 77.1%).

The reaction product was subjected to distillation under reduced pressure under conditions where the internal pressure was 0.2 kPa, the internal temperature was 104 to 119° C., and the overhead temperature was 84 to 85° C. Thus, 36 g of purified reaction product (98.0GC %) was obtained (distillation yield: 41.6%). The results of $^1$H-NMR and $^{19}$F-NMR confirmed that this purified reaction product was a mixture of compounds represented by the following formulae:

$^1$H-NMR (CDCl$_3$, TMS):
δ5.11-5.81 (CH=CF, CF=CH)
2.26-2.42 (CH$_2$CH$_2$)
3.95 (CH$_2$CH$_2$)
3.02-3.21 (OH)
$^{19}$F-NMR (CDCl$_3$, C$_6$F$_6$):
ppm −87.0 to −86.6 (CF$_3$)
 −118.0 to −109.6 (CF$_2$CH=CF, CF=CHCF$_2$)
 −120.1 to −119.3 (CF$_2$CF$_2$CF$_2$CF$_2$CH$_2$)
 −123.4 to −122.1 (CF$_2$CF$_2$CF$_2$CF$_2$CH$_2$)
 −124.6 (CF$_2$CF$_2$CF$_2$CF$_2$CH$_2$)
 −114.2 (CF$_2$CF$_2$CF$_2$CF$_2$CH$_2$)

Example 5

The mixture of compounds (98.0GC %) obtained in Reference Example 4 (2) (35 g; 0.08 mol), 22 g of toluene, 7 g of p-toluenesulfonic acid, and 0.4 g of hydroquinone were charged in a four-necked 100-ml flask equipped with a condenser, thermometer, and stirrer. After the internal temperature was raised to 100° C., 8 g (0.11 mol) of acrylic acid was added, and the mixture was stirred for reaction at an internal temperature of 115° C. for 4 hours. After the completion of the reaction, the toluene was removed by an evaporator from 72 g of the reaction mixture solution obtained by cooling, and 52 g of residue was washed with tap water. Thus, 42 g of reaction product (87.9GC %), which was a light-yellow, transparent liquid at ambient temperature, was obtained (yield: 85.8%).

The reaction product was subjected to distillation under reduced pressure under conditions where the internal pressure was 0.1 kPa, the internal temperature was 124 to 128° C., and the overhead temperature was 63 to 68° C. Thus, 30 g of purified reaction product (98.8GC %) was obtained (distillation yield: 79.1%). The results of $^1$H-NMR and $^{19}$F-NMR confirmed that this purified reaction product was a mixture of compounds represented by the following formulae:

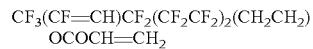

$^1$H-NMR (CDCl$_3$, TMS):
δ5.70-5.83 (CH=CF, CF=CH)
2.46 (CH$_2$CH$_2$)
4.43 (CH$_2$CH$_2$)
6.14 (CH=CH$_2$)
6.41, 5.8 (CH=CH$_2$)
$^{19}$F-NMR (CDCl$_3$, C$_6$F$_6$):
ppm −87.0 to −86.7 (CF$_3$)
 −117.6 to −110.4 (CF$_2$CH=CF, CF=CHCF$_2$)
 −122.1 to −120.3 (CF$_2$CF$_2$CF$_2$CF$_2$CH$_2$)
 −123.8 to −122.5 (CF$_2$CF$_2$CF$_2$CF$_2$CH$_2$)
 −124.8 (CF$_2$CF$_2$CF$_2$CF$_2$CH$_2$)
 −114.5 (CF$_2$CF$_2$CF$_2$CF$_2$CH$_2$)

Reference Example 5

(1) A compound of the formula: CF$_3$CF$_2$(CH$_2$CF$_2$)(CF$_2$CF$_2$)I (99.8GC %) (610 g; 1.48 mol) and 7 g of di-tert-butyl peroxide were charged in a 1200-ml autoclave equipped with a stirrer and thermometer, and the autoclave was degassed by a vacuum pump. After the internal temperature was raised to 80° C., ethylene was sequentially introduced so that the internal pressure was 0.5 MPa. When the internal pressure decreased to 0.2 MPa, ethylene was introduced again to return the pressure to 0.5 MPa; this operation was repeated. While maintaining the internal temperature at 80 to 115° C., 62 g (2.23 mol) of ethylene was introduced over about 3 hours. The content was collected at an internal temperature of 50° C. or less, thereby obtaining 644 g of compound of the formula: CF$_3$CF$_2$(CH$_2$CF$_2$)(CF$_2$CF$_2$)(CH$_2$CH$_2$)I (98.7GC %) (yield: 98.0%).

(2) The compound of the formula: CF$_3$CF$_2$(CH$_2$CF$_2$)(CF$_2$CF$_2$)(CH$_2$CH$_2$)I (98.7GC %) (150 g; 0.34 mol) obtained above (1) and 251 g (4.26 mol) of N-methylformamide were charged in a four-necked 300-ml flask equipped with a condenser, thermometer, and stirrer, and the mixture was stirred and reacted at 150° C. for 8 hours. After the completion of the reaction, the reaction mixture was washed with 100 ml of water, and 130 g of lower layer of the mixture was mixed with 135 g of a 10 wt. % NaOH aqueous solution, followed by reaction under stirring at 90° C. for 8 hours. After the reaction mixture was allowed to stand, 119 g of reaction product (68.8GC %), which was light-yellow, transparent liquid at ambient temperature, was obtained as the lower layer of the mixture (yield: 78.2%).

The reaction product was subjected to distillation under reduced pressure under conditions where the internal pressure was 0.2 kPa, the internal temperature was 100 to 114° C., and the overhead temperature was 80 to 81° C. Thus, 38 g of purified reaction product (98.1GC %) was obtained (distillation yield: 45.3%). The results of $^1$H-NMR and $^{19}$F-NMR confirmed that this purified reaction product was a mixture of compounds represented by the following formulae:

$^1$H-NMR (CDCl$_3$, TMS):
δ5.09-5.77 (CH=CF, CF=CH)
2.21-2.36 (CH$_2$CH$_2$)
3.91 (CH$_2$CH$_2$)
3.55-3.68 (OH)
$^{19}$F-NMR (CDCl$_3$, C$_6$F$_6$):
ppm −87.0 to −86.6 (CF$_3$)
−118.0 to −109.5 (CF$_2$CH=CF, CF=CHCF$_2$)
−124.6 (CF$_2$CF$_2$CH$_2$)
−114.2 (CF$_2$CF$_2$CH$_2$)

Example 6

The mixture of compounds (98.1GC %) obtained in Reference Example 5 (2) (37 g; 0.12 mol), 26 g of toluene, 8 g of p-toluenesulfonic acid, and 0.4 g of hydroquinone were charged in a four-necked 100-ml flask equipped with a condenser, thermometer, and stirrer. After the internal temperature was raised to 100° C., 11 g (0.15 mol) of acrylic acid was added, and the mixture was stirred for reaction at an internal temperature of 115° C. for 4 hours. After the completion of the reaction, the toluene was removed by an evaporator from 81 g of the reaction mixture solution obtained by cooling, and 58 g of residue was washed with tap water. Thus, 45 g of reaction product (89.2GC %), which was light-yellow, transparent liquid at ambient temperature, was obtained (yield: 87.5%).

The reaction product was subjected to distillation under reduced pressure under conditions where the internal pressure was 0.1 kPa, the internal temperature was 120 to 124° C., and the overhead temperature was 59 to 63° C. Thus, 34 g of purified reaction product (98.9GC %) was obtained (distillation yield: 83.0%). The results of $^1$H-NMR and $^{19}$F-NMR confirmed that this purified reaction product was a mixture of compounds represented by the following formulae:

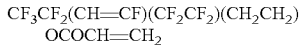

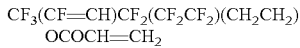

$^1$H-NMR. (CDCl$_3$, TMS):
δ5.67-5.81 (CH=CF, CF=CH)
2.45 (CH$_2$CH$_2$)
4.37 (CH$_2$CH$_2$)
6.11 (CH=CH$_2$)
6.40, 5.88 (CH=CH$_2$)
$^{19}$F-NMR (CDCl$_3$, C$_6$F$_6$):
ppm −87.0 to −86.7 (CF$_3$)
−117.6 to −110.4 (CF$_2$CH=CF, CF=CHCF$_2$)
−124.8 (CF$_2$CF$_2$CH$_2$)
−114.5 (CF$_2$CF$_2$CH$_2$)

Example 7

The mixture of fluoroalkyl alcohol acrylic acid derivatives (98.0GC %) represented by the formulae: CF$_3$(CF$_2$)$_3$(CH=CF)(CF$_2$CF$_2$)$_2$(CH$_2$CH$_2$) OCOCH=CH$_2$ and CF$_3$(CF$_2$)$_2$(CF=CH)CF$_2$(CF$_2$CF$_2$)$_2$(CH$_2$CH$_2$)OCOCH=CH$_2$, which was the purified reaction product obtained in Example 1 (10 g), 35 g of 1,4-bis(trifluoromethyl)benzene, and 0.16 g of bis(4-tert-butylcyclohexyl)-peroxydicarbonate were charged in a 50-ml eggplant type flask equipped with a condenser, and while stirring with a magnet stirrer, a polymerization reaction was carried out at 50° C. for 16 hours. Thus, a polymer solution having a solid matter content of 21.6 wt. % was obtained. The polymer solution was diluted with 1,4-bis(trifluoromethyl)benzene to a solid matter content of 2 wt. %.

The diluted solution (1 ml) was applied to a stainless steel plate (2×5 cm) and dried at 50° C. for 30 minutes, thereby producing a test piece.

Here, the used polymer solution was placed in an oven at 120° C. to remove the solvent, so that the fluorine-containing polymer was isolated. The weight average molecular weight Mw of the polymer was measured, and the result was 35,000. The weight average molecular weight Mw was measured by GPC using Shodex GPC KD806M+KD-802+KD-G at a temperature of 40° C. under the condition where the elution rate of 10 mM THF (i.e., eluate) was 1 ml/min. The detector used was a differential refractive index detector, and the analysis was conducted using Labchat 180 (manufactured by SIC) in terms of polystyrene.

Example 8

In Example 7, the mixture of fluoroalkyl alcohol-acrylic acid derivatives, which was the purified reaction product obtained in Example 2, was used as a mixture of fluoroalkyl alcohol-unsaturated carboxylic acid derivatives. Thus, a polymer solution was produced, and then a test piece was prepared. Here, the solid matter content of the polymer solution was 21.4 wt. %, and the weight average molecular weight Mw of the polymer was 45,000.

Example 9

In Example 7, the mixture of fluoroalkyl alcohol-acrylic acid derivatives, which was the purified reaction product obtained in Example 3, was used as a mixture of fluoroalkyl alcohol-unsaturated carboxylic acid derivatives. Thus, a polymer solution was produced, and then a test piece was prepared. Here, the solid matter content of the polymer solution was 21.1 wt. %, and the weight average molecular weight Mw of the polymer was 35,000.

Example 10

In Example 7, the mixture of fluoroalkyl alcohol-methacrylic acid derivatives, which was the purified reaction product obtained in Example 4, was used as a mixture of fluoroalkyl alcohol-unsaturated carboxylic acid derivatives. Thus, a polymer solution was produced, and then a test piece was prepared. Here, the solid matter content of the polymer solution was 20.7 wt. %, and the weight average molecular weight Mw of the polymer was 20,000.

Comparative Reference Examples 1 to 3

In Example 7, a compound of the formula: C$_4$F$_9$(CH$_2$CH$_2$)OCOCH=CH$_2$ (Comparative Reference Example 1), C$_6$F$_{13}$(CH$_2$CH$_2$)OCOCH=CH$_2$ (Comparative Reference Example 2), or C$_8$F$_{17}$(CH$_2$CH$_2$)OCOCH=CH$_2$ (Comparative Reference Example 3) was used in the same amount in place of the mixture of fluoroalkyl alcohol-unsaturated carboxylic acid derivatives obtained in Example 1. Thus, polymer solutions were produced, and then test pieces were prepared. Here, the solid matter content of each polymer solution was 21.0 wt. %.

As for the test pieces obtained in Examples 7 to 10 and Comparative Reference Examples 1 to 3, their static contact angles, which were an indicator of water- and oil-repellent performance, were measured by the sessile-drop method using various organic solvents and water. The obtained results are shown in the following Table. It was confirmed that the static contact angles of the test pieces of the Examples were equivalent to that of Comparative Reference Example 3 (n=8).

TABLE

| Example | Heptane | Octane | Decane | Dodecane | Tetra-decane | Water |
|---|---|---|---|---|---|---|
| Ex. 7 | 57° | 60° | 65° | 70° | 73° | 119° |
| Ex. 8 | 56° | 59° | 64° | 70° | 74° | 118° |
| Ex. 9 | 57° | 59° | 64° | 69° | 72° | 119° |
| Ex. 10 | 57° | 60° | 65° | 69° | 73° | 120° |
| Comp. Ref. Ex. 1 | 36° | 40° | 52° | 59° | 71° | 114° |
| Comp. Ref. Ex. 2 | 42° | 48° | 56° | 64° | 79° | 118° |
| Comp. Ref. Ex. 3 | 58° | 60° | 66° | 72° | 78° | 120° |

Example 11

The mixture of fluoroalkyl alcohol-acrylic acid derivatives (98.0GC %) represented by the formulae: $CF_3(CF_2)_3(CH=CF)(CF_2CF_2)_2(CH_2CH_2)OCOCH=CH_2$ and $CF_3(CF_2)_2(CF=CH)CF_2(CF_2CF_2)_2(CH_2CH_2)OCOH=CH_2$, which was the purified reaction product obtained in Example 1, (73.0 g; 0.130 mol), 6.0 g of 2-hydroxyethyl acrylate, 22.0 g of benzyl methacrylate, 4.0 g of polyalkyleneglycol monomethacrylate, 7.0 g of polyoxyethylene alkyl ether, 80.0 g of acetone, 0.5 g of n-dodecyl mercaptan (molecular weight modifier), and 220.0 g of water were charged in a 500-ml glass reactor, and the mixture was emulsified under 60 MPa of pressure using a high-pressure homogenizer. Subsequently, the obtained emulsified liquid was replaced by nitrogen gas for 30 minutes, and an aqueous solution containing 11.0 g of vinylidene chloride, 6.0 g of N-methylolacrylamide, 2.5 g of 2,2'-azobis(2-amidinopropane)dihydrochloride (radical polymerization initiator), and 30.0 g of water was supplied, followed by reaction at 70° C. for 4 hours. After the reaction, the resultant was cooled, thereby obtaining 485 g of aqueous dispersion having a solid matter content of 25.0%. Mw of the obtained fluorine-containing polymer was 40,000.

Example 12

In Example 11, 60.0 g (0.130 mol) of the mixture of fluoroalkyl alcohol-acrylic acid derivatives, which was the purified reaction product obtained in Example 2, was used as a mixture of fluoroalkyl alcohol-unsaturated carboxylic acid derivatives. Thus, 471 g of aqueous dispersion having a solid matter content of 24.8% was obtained. Mw of the obtained fluorine-containing polymer was 50,000.

Example 13

In Example 11, 73.0 g (0.130 mol) of the mixture of fluoroalkyl alcohol-acrylic acid derivatives, which was the purified reaction product obtained in Example 3, was used as a mixture of fluoroalkyl alcohol-unsaturated carboxylic acid derivatives. Thus, 484 g of aqueous dispersion having a solid matter content of 25.1% was obtained. Mw of the obtained fluorine-containing polymer was 40,000.

Example 14

In Example 11, 74.9 g (0.130 mol) of the mixture of fluoroalkyl alcohol-methacrylic acid derivatives, which was the purified reaction product obtained in Example 4, was used as a mixture of fluoroalkyl alcohol-unsaturated carboxylic acid derivatives. Thus, 486 g of aqueous dispersion having a solid matter content of 24.5% was obtained. Mw of the obtained fluorine-containing polymer was 25,000.

Comparative Reference Example 4

In Example 11, 65.0 g (0.125 mol) of compound of the formula: $CF_3(CF_2)_7(CH_2CH_2)OCOCH=CH_2$ was used in place of the mixture of fluoroalkyl alcohol-acrylic acid derivatives obtained in Example 1. Thus, 452 g of aqueous dispersion having a solid matter content of 21.0% was obtained.

Comparative Example 1

In Example 11, 52.0 g (0.125 mol) of compound of the formula: $CF_3(CF_2)_5(CH_2CH_2)OCOCH=CH_2$ was used in place of the mixture of fluoroalkyl alcohol-acrylic acid derivatives obtained in Example 1. Thus, 466 g of aqueous dispersion having a solid matter content of 22.7% was obtained.

Comparative Example 2

In Example 11, 40.0 g (0.125 mol) of compound of the formula: $CF_3(CF_2)_3(CH_2CH_2)OCOCH=CH_2$ was used in place of the mixture of fluoroalkyl alcohol-acrylic acid derivatives obtained in Example 1. Thus, 480 g of aqueous dispersion having a solid matter content of 24.4% was obtained.

The aqueous dispersions obtained in Examples 11 to 14, Comparative Reference Example 4, and Comparative Examples 1 and 2 were diluted with water to a solid matter content of 0.5 wt. %. Then, cotton cloth, cotton/polyester mixed cloth, polyester cloth and nylon cloth were each immersed therein, and water-repellent performance (according to JIS L1092) and oil-repellent performance (according to AATCC-TM118) were measured. The wet pickup after squeezing was as follows: cotton cloth: 110%, cotton/polyester mixed cloth: 75%, polyester cloth: 115%, and nylon cloth: 45%. The drying was performed at 80° C. for 10 minutes, and the cure was performed at 150° C. for 3 minutes for the cotton cloth, cotton/polyester mixed cloth, and polyester cloth; and at 170° C. for 1.5 minutes for the nylon cloth.

The obtained results are shown in Table 1 (water-repellent performance) and Table 2 (oil-repellent performance) below.

TABLE 1

| Water-repellent performance | Ex. | | | | Com. Ref. Ex. | Comp. Ex. | |
|---|---|---|---|---|---|---|---|
|  | 11 | 12 | 13 | 14 | 4 | 1 | 2 |
| Cotton | 100 | 90 | 100 | 100 | 100 | 70 | 70 |
| Cotton/polyester | 100 | 100 | 100 | 100 | 100 | 80 | 50 |
| Polyester | 100 | 100 | 100 | 100 | 100 | 70 | 70 |
| Nylon | 100 | 100 | 100 | 100 | 100 | 80 | 70 |

TABLE 2

| Oil-repellent performance | Ex. 11 | Ex. 12 | Ex. 13 | Ex. 14 | Com. Ref. Ex. 4 | Comp. Ex. 1 | Comp. Ex. 2 |
|---|---|---|---|---|---|---|---|
| Cotton | 6 | 6 | 6 | 6 | 6 | 5 | 4 |
| Cotton/polyester | 7 | 7 | 7 | 7 | 7 | 5 | 4 |
| Polyester | 6 | 6 | 6 | 6 | 6 | 5 | 4 |
| Nylon | 7 | 7 | 7 | 7 | 7 | 7 | 5 |

The invention claimed is:

1. A mixture of fluoroalkyl alcohol-unsaturated carboxylic acid derivatives represented by the general formulae:

$$CF_3(CF_2)_n(CH=CF)_a(CF_2CF_2)_b(CH_2CH_2)_cOCOCR=CH_2 \quad \text{(Ia)}$$

and $$CF_3(CF_2)_{n-1}(CF=CH)_aCF_2(CF_2CF_2)_b(CH_2CH_2)_cOCOCR=CH_2 \quad \text{(Ib)}$$

wherein R is a hydrogen atom or a methyl group, n is an integer of 1 to 5, a is an integer of 1 to 4, b is an integer of 0 to 3, and c is an integer of 1 to 3.

2. A method for producing a mixture of fluoroalkyl alcohol unsaturated-carboxylic acid derivatives represented by the general formulae:

$$CF_3(CF_2)_n(CH=CF)_a(CF_2CF_2)_b(CH_2CH_2)_cOCOCR=CH_2 \quad \text{(Ia)}$$

and $$CF_3(CF_2)_{n-1}(CF=CH)_aCF_2(CF_2CF_2)_b(CH_2CH_2)_cOCOCR=CH_2 \quad \text{(Ib)}$$

wherein R is a hydrogen atom or a methyl group, n is an integer of 1 to 5, a is an integer of 1 to 4, b is an integer of 0 to 3, and c is an integer of 1 to 3; which method comprises subjecting to an esterification reaction of a mixture of fluoroalkyl alcohol represented by the general formulae:

$$CF_3(CF_2)_n(CH=CF)_a(CF_2CF_2)_b(CH_2CH_2)_cOH \quad \text{[IIa]}$$

and $$CF_3(CF_2)_{n-1}(CF=CH)_aCF_2(CF_2CF_2)_b(CH_2CH_2)_cOH \quad \text{[IIb]}$$

wherein n, a, b and c are as defined above; with acrylic acid or methacrylic acid.

3. The method according to claim 2, wherein the esterification reaction is carried out in the presence of a p-toluenesulfonic acid catalyst.

4. A fluorine-containing polymer containing as a polymerization unit a mixture of fluoroalkyl alcohol-unsaturated carboxylic acid derivatives represented by the general formulae:

$$CF_3(CF_2)_n(CH=CF)_a(CF_2CF_2)_b(CH_2CH_2)_cOCOCR=CH_2 \quad \text{(Ia)}$$

and $$CF_3(CF_2)_{n-1}(CF=CH)_aCF_2(CF_2CF_2)_b(CH_2CH_2)_cOCOCR=CH_2 \quad \text{(Ib)}$$

wherein R is a hydrogen atom or a methyl group, n is an integer of 1 to 5, a is an integer of 1 to 4, b is an integer of 0 to 3, and c is an integer of 1 to 3.

5. The fluorine-containing polymer according to claim 4, wherein the mixture of fluoroalkyl alcohol-unsaturated carboxylic acid derivatives is copolymerized with a polyfluoroalkyl group-containing (meth)acrylic monomer represented by the general formulae:

$$CH_2=CRCOOR_1(NR_2SO_2)_mRf$$

wherein R is a hydrogen atom or a methyl group, $R_1$ is a divalent organic group having 1 to 4 carbon atoms, $R_2$ is a lower alkyl group having 1 to 5 carbon atoms, Rf is a polyfluoroalkyl group having 1 to 6 carbon atoms, and m is 0 or 1; and/or fluorine-free polymerizable monomer.

6. The fluorine-containing polymer according to claim 5, wherein in the polyfluoroalkyl group-containing (meth)acrylate monomer to be copolymerized with the mixture of fluoroalkyl alcohol-unsaturated carboxylic acid derivatives, where $R_1$ if a polyfluoroalkylene group, the total number of carbon atoms in the polyfluoroalkylene group and terminal polyfluoroalkyl group is 1 to 6.

7. A water- and oil-repellent comprising the fluorine-containing polymer of claim 4 as an active ingredient.

8. The water- and oil-repellent according to claim 7, which is prepared as an organic solvent solution.

9. The water- and oil-repellent according to claim 8, wherein the organic solvent is a fluorine-containing organic solvent.

10. An aqueous dispersion of the fluorine-containing polymer of claim 4.

11. A water- and oil-repellent comprising the fluorine-containing polymer aqueous dispersion of claim 10.

12. The water- and oil-repellent according to claim 11, wherein the fluorine-containing polymer has a solid matter content of 0.1 to 10 wt. %.

* * * * *